(12) United States Patent
Levine

(10) Patent No.: US 7,467,537 B2
(45) Date of Patent: Dec. 23, 2008

(54) SEAM ABRASION TESTING DEVICE AND METHOD OF USE

(75) Inventor: Serge Levine, Hickory, NC (US)

(73) Assignee: BSN Medical, Inc., Charlotte, NC (US)

( * ) Notice: Subject to any disclaimer, the term of this patent is extended or adjusted under 35 U.S.C. 154(b) by 388 days.

(21) Appl. No.: 11/267,416

(22) Filed: Nov. 4, 2005

(65) Prior Publication Data

US 2007/0119245 A1 May 31, 2007

(51) Int. Cl.
*G01N 3/56* (2006.01)

(52) U.S. Cl. .............................. 73/7; 73/159

(58) Field of Classification Search ............. 73/7, 73/159; 623/64
See application file for complete search history.

(56) References Cited

U.S. PATENT DOCUMENTS

| | | | |
|---|---|---|---|
| 1,632,591 A | | 6/1927 | Dennis |
| 2,464,577 A | * | 3/1949 | Hobbs ................... 623/63 |
| 2,670,627 A | | 3/1954 | Shaw |
| 3,694,021 A | | 9/1972 | Mullen |
| 4,094,016 A | | 6/1978 | Eroyan |
| 4,136,557 A | | 1/1979 | Bell, Jr. et al. |
| 4,834,443 A | * | 5/1989 | Crowder et al. ............. 294/106 |
| 4,946,380 A | * | 8/1990 | Lee ............................ 623/24 |
| 5,004,391 A | * | 4/1991 | Burdea ....................... 414/6 |
| 5,052,736 A | * | 10/1991 | Loncaric et al. ............. 294/106 |
| 5,080,681 A | | 1/1992 | Erb |
| 5,080,682 A | * | 1/1992 | Schectman ................. 623/64 |
| 5,200,679 A | * | 4/1993 | Graham .................. 318/568.16 |
| 6,019,259 A | | 2/2000 | Staniecki |
| 6,312,398 B1 | | 11/2001 | Cencer |
| 6,817,641 B1 | * | 11/2004 | Singleton, Jr. ............. 294/106 |
| 6,913,627 B2 | * | 7/2005 | Matsuda ..................... 623/64 |

FOREIGN PATENT DOCUMENTS

| | | |
|---|---|---|
| JP | 58167960 A | 10/1983 |
| JP | 62195537 A | 8/1987 |

\* cited by examiner

*Primary Examiner*—Hezron E. Williams
*Assistant Examiner*—John Fitzgerald
(74) *Attorney, Agent, or Firm*—Adams Intellectual Property Law PA

(57) ABSTRACT

There is provided a testing device for testing the seam of a garment that includes a mechanical abrader frame holding elongate members and a control unit. The mechanically oscillating elongate members are each connected to an actuator located within the frame. A test sample is placed on the elongate members of the mechanical abrader frame. Actuators are attached to the connection rods that extend through openings in the front wall of the frame and attach to each of the elongate members for imparting extending and retracting movement to the elongate member. Each of the actuators has an attachment member affixed to its rear end that permits a support rod to pass therethrough allowing for a degree of rotation about the support rod as the connection rod is extended and retracted. A control unit regulates movement of the elongate members and determines the number of revolutions of the elongate members. A method for testing the seam abrasion of a garment seam is also provided.

11 Claims, 2 Drawing Sheets

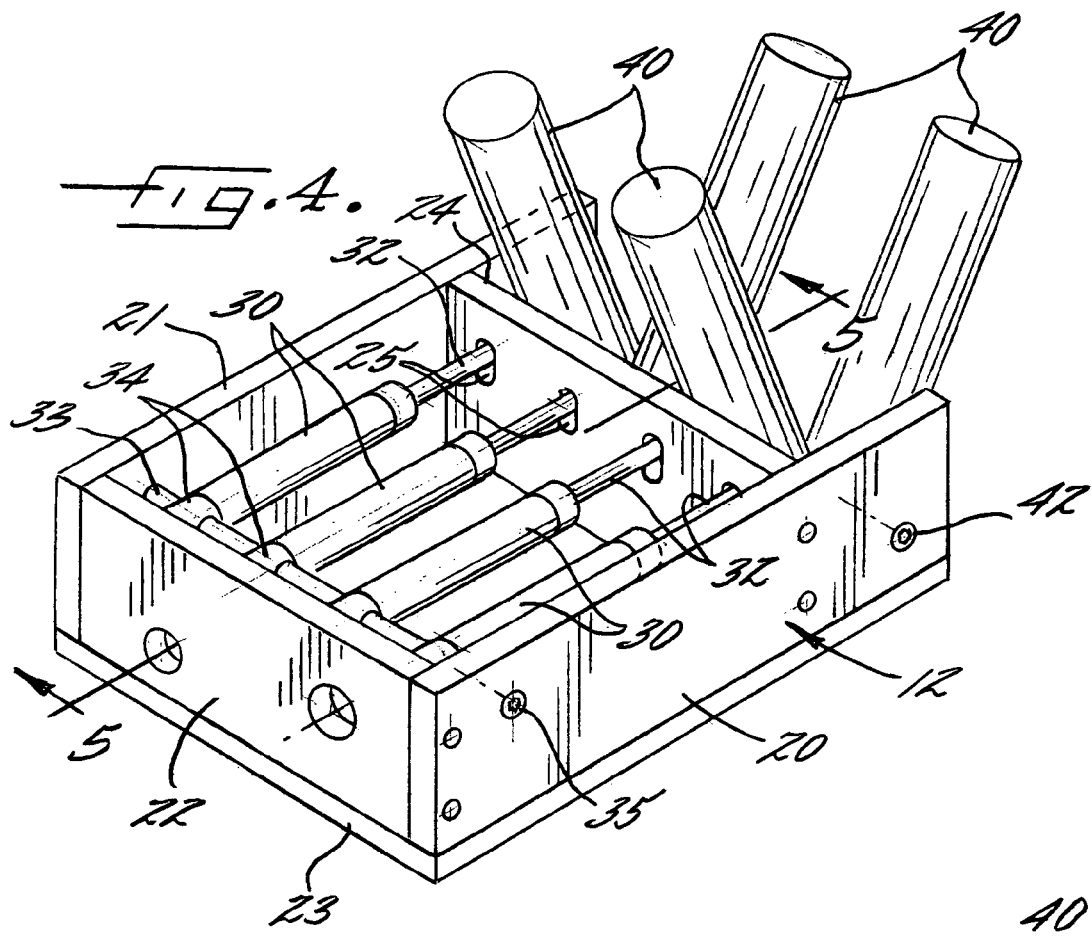
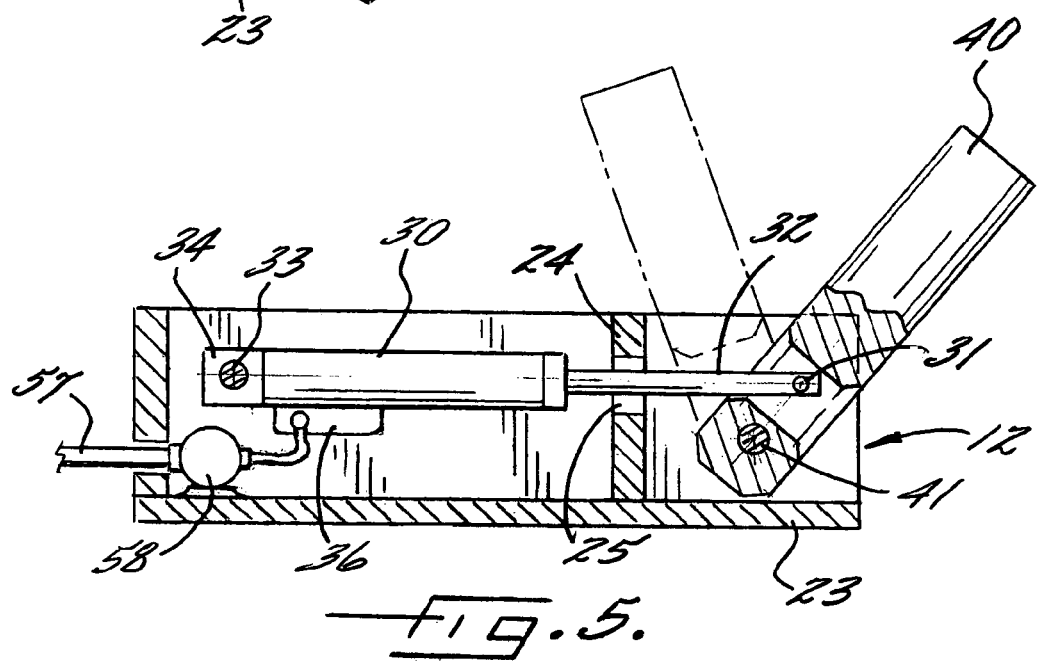

SEAM ABRASION TESTING DEVICE AND METHOD OF USE

BACKGROUND OF THE INVENTION

1. Field of the Invention

The present invention generally relates to a device for testing seam abrasion and a method of using the device. More particularly, the invention relates to a testing device having oscillating finger-like members and a method for testing wear conditions at the seams of garments that are similar to the wear patterns of the user.

2. Description of Related Art

Garments wear out in both the fabric area and at the seams. During wear imposed by a given seam, deterioration manifests prior to the seams' full destruction. While the physical properties of the seam, such as strength and elongation, do not change greatly until the complete seam failure occurs, the garment, in this case a glove, is aesthetically displeasing. The type of wear applied by a testing device to the seams of a glove differs from the wear applied by available fabric abrading testers. For example, testing devices developed for wearing out fabrics apply wear to a flat surface. Generally the amount of cycles it takes to rub a hole through a flat piece of fabric by a given abrasion defines its durability. However, seams behave differently during wear, and subjecting them to the same test conditions reveals misleading information.

Two major factors contribute to durability of seams. First, abrasion resistance of the thread, and second, abrasion resistance properties of the seam. Testing durability of the thread does not necessarily define the true characteristic of the seam. Seam type, machine settings and stitch density have significant affect on a seam's durability. Common abrading devices are designed to apply wear to a flat surface; however, not all seams may be sewn on a flat piece of fabric. Some, such as edge finishing seams, need to be sewn on the edge of the fabric.

Fabric abrasion testing, as opposed to seam abrasion testing, has been conducted for many years. For example, U.S. Pat. No. 1,632,591 to Dennis discloses a fabric abrasion tester for determining the wear resisting qualities of products such as textiles, threads, or yarns. The fabric abrasion tester indicates the extent of wearing or frictional action required for wearing through the fabric by providing a device in the form of a register or counter. The fabric abrasion tester includes a roll having an abrasive cover that is rotated against a sample of fabric. The fabric is held in place against the roll under tension. The rotary motion imparted to the roll provides a wearing action on a portion of the fabric. A register or indicating means, which measures the extent of frictional wear, is provided. In that way, the number of revolutions of the roll are registered indicating the extent of action required for wearing through a particular piece of fabric.

Another example of a fabric testing device, U.S. Pat. No. 2,670,627 to Shaw, discloses an apparatus for testing the resistance of textile fabric to abrasion, flexing and creasing. This apparatus comprises two rolls arranged in such manner that the surfaces of rotation of the rolls are parallel. One roll holds strips of material to be tested and the other roll carries suitable abrasive material for abrading the material to be tested. The invention is said to be especially useful for testing the wearability of asbestos textiles and other fabrics of heavier grades. According to the specification, it may be desired to use as an abradant a strip of fabric of the same character as that being tested. Preferably, one roll is substantially larger than the other roll.

Testing seams in garments and damage to garment fabrics is the subject of U.S. Pat. No. 4,136,557 to Bell, Jr., et al. A pantyhose testing apparatus is provided in which a mannequin conforming substantially to the lower portion of a human torso is provided with waist, leg and hip portions for receiving thereon a pantyhose garment. A pantyhose garment is placed on the mannequin and stretched until damage occurs. A gauge measures the force necessary to initiate damage to the garment. In testing garment's resistance to seam burst and/or fabric damage, the electrical circuit is energized through a switch and fluid under pressure is directed to cylinders such that the initial clamps are in the open position and the displaced crotch member is positioned in abutting relation with the mannequin crotch area. Actuating the switch activates the solenoid displacing a valve such as the fluid pressure closes the clamps and secures the garment adjacent the mannequin waist portion. The crotch member presses against the crotch area of the garment clamped upon the mannequin and the member continues to move away from the mannequin body portion until such time that the garment is damaged. A gauge records the force necessary to burst a garment seam or otherwise damage the garment and gives an indication of the resistance or force comparable garments will afford to forces tending to damage the garment.

Finger actuated devices are known from U.S. Pat. No. 6,312,398 to Cencer. That hand-like device includes a power assisted actuator assembly for flexing restraints in response to the movement of the underlying member or controller, e.g., a hand. The actuator assembly generally includes a flexible member such as a cord or fabric panel having a flat end coupled to the resistant and a second end coupled to a driver member. The actuator assembly comprises part of a glove and as the glove becomes more conformal to the human joint, the motion of restraint occurs substantially simultaneously with the motion of the human joint.

Although fabric abrasion testing devices are known from the prior art, devices designed specifically to test seams in gloves are not known. Thus, it is highly desirable to provide a device for determining the seam abrasion of a glove.

It is a general object of the present invention to provide a device for testing the seam wear of a garment that are similar to the wear patterns of the end user. Another object of the present invention is to provide a method for testing the seam wear of a glove. It is a further object of the invention to provide a simple testing device that includes finger-like elongate members, placing a glove thereon and simulating seam wear by oscillating the elongate members and to obtain the seam abrasion results.

BRIEF SUMMARY OF THE INVENTION

The above and other objects and advantages of the invention are achieved by the provision of a testing device, which, in general, includes a mechanical abrader frame holding elongate member and a control unit for controlling the movement of the elongate member. A test sample is sewn according to a predetermined template and instructions, using the thread and seams to be tested and then placed on the elongate members.

The frame has a base and a pair of side walls, a front wall and a rear wall. There are four mechanically oscillating elongate members, each representing the finger of a hand, connected to an actuator. The front wall has a plurality of openings of such size that connection rods may pass therethrough. Actuators are attached to the connection rods that extend through openings in the front wall of the frame and attach to each of the elongate members for imparting extending and retracting movement to the elongate member. Each of the actuators is activated by a solenoid and has an attachment member affixed to its rear end that permits a support rod to pass therethrough allowing for a degree of rotation about the support rod as the connection rod is extended and retracted. The actuators are connected to a control unit and are operated either simultaneously or individually to extend and retract movement of the elongate members. The control unit provides for regulating the movement of the elongated members and determining the number of revolutions of the elongate members. The control unit includes a speed regulating means, gauge for adjusting the speed of the elongated members. The control unit also includes means for recording the number of oscillations applied to the elongated members sufficient to determine damage to a seam.

A method for testing the seam abrasion of a glove seam is provided by placing a sample glove on a plurality of moveable finger-like elongate members for supporting a glove, oscillating the elongate members by imparting extending and retracting movement thereto, controlling the oscillated elongate members by regulating the movement of the elongated members; and determining the amount of wear on the seam of said glove. Using the interactive display the operator inputs the amount of cycles to be executed on the sample. The device then executes the entered amount of cycles by rubbing the seams against one another and against the fabric. Then the wear is compared to a "pass" or "fail" sample for evaluation of competency of the seam.

Thus, with the present invention there is provided a testing device and control unit for regulating the testing device that is easy to use, simple in operation and measures wear of a sewn seam.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 4 is a perspective view of seam tester frame and digits of the present invention; and FIG. 5 is a vertical cutaway section view of the testing device of the present invention taken along line 5-5 of FIG. 5.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The seam abrader is a testing device which creates wear conditions which are similar to those of the end user. The device was developed specifically for testing "seams" of garments while other abraders on the market are designed for testing "textiles" and thread. The type of wear applied by the device to the seams differs from the wear applied by available abrading devices. Namely, abraders developed for wearing out fabrics apply wear to a flat surface. Generally the amount of cycles it takes to rub a hole through a flat piece of fabric by a given abrasion defines its durability. However, seams behave differently during wear, and subjecting them to the same test conditions reveals misleading information. Seam abrader is designed to apply gentler force over greater amount of cycles which permits determination of the durability of the seam accurately. The applied force separates the filaments of the thread instead of destroying them, which is the effect produced by the common abrading devices. This feature is especially effective in testing of seams constructed with textured threads.

Figure 1:
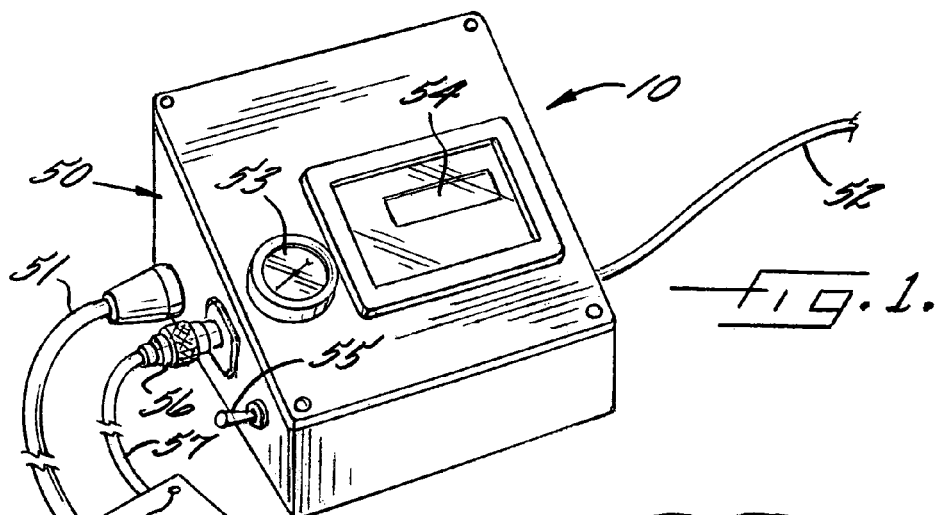
FIG. 1 is an environmental view illustrating the seam testing device of this invention showing the testing frame and the control unit.
Figure 2:
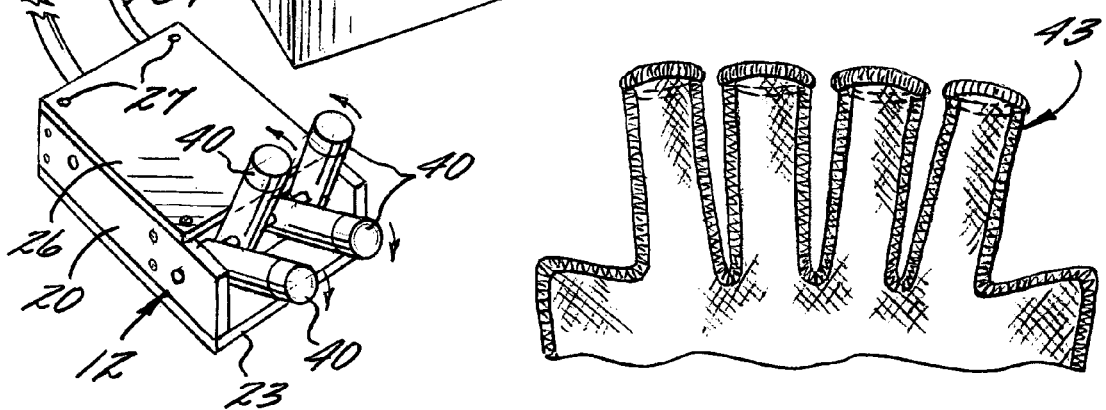
FIG. 2 illustrates a simulated glove, with the finger tips removed, ready to be placed on the elongated members for testing.
Figure 3:
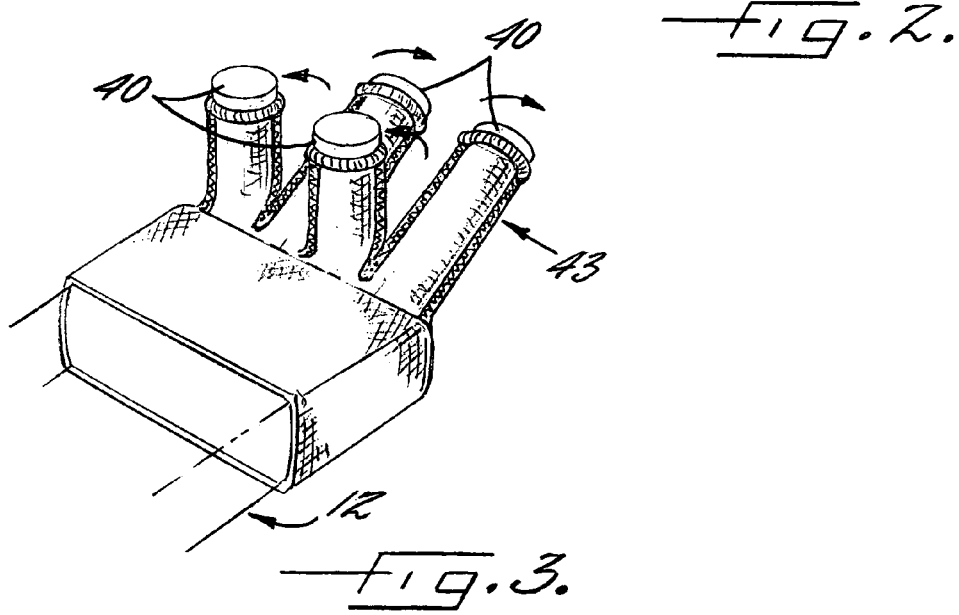
FIG. 3 illustrates the glove placed on the elongated members of the testing device.

The seam abrader comprises a series of mechanical oscillating fingers. A test sample, such as shown in FIG. 2, is sewn according to a predetermined template and instructions, using the thread and seams to be tested. The test sample is then placed on the mechanical abrader as shown in FIG. 3. Referring more particularly to the drawings, FIG. 1 shows the testing device 10 of the present invention. The device 10 for testing the abrasion of the seams of a glove includes a frame 12 and a control unit 50. As shown in FIG. 4, the frame 12 of seam testing device 10, as shown most clearly in FIG. 4, comprises a base 23 and a pair of side walls 20, 21 respectively. The frame includes a front wall 24 and a rear wall 22. The front wall 24 has a plurality of openings 25 of such size that connector rods 32 may pass therethrough. Front wall 24 is preferably somewhat thicker than the remaining walls. Preferably the frame 12 also includes a planar cover 26 removably secured to the frame by fasteners 27, such as screws. The frame 12 may be made of metal or plastic.

A plurality of moveable finger-like elongate members 40 are provided to support a sample test glove 43 during testing. In the testing device shown in FIGS. 4 and 5 the elongate member 40 is connected to an actuating member 30 by connecting rods 32. As shown, there are four elongate members 40, each representing the finger of a hand. The glove 43 is placed over the digits of the elongate members. The elongate members 40 are supported in frame 12 by support rod 41 attached to frame 12 by connector rod pin 42. The support rod 41 is smaller than the holes through the lower end of the elongated member 40 to allow the elongate member to extend and retract as the connector rod 32 moves.

Each of the actuators 30 are attached to a connection rod 32 that extends through an opening 25 in the front wall 24 of frame 12 and attaches at 31 to one of the elongate members 40 for imparting extending and retracting movement to said elongate member. For example, in some embodiments the actuator 30 is pneumatic. It should be understood that an electric or hydraulic actuator or a motor may be used. Each of the actuating members 30 has an actuator connector 34 affixed to its rear end that permits a support rod 33 to pass therethrough allowing for a degree of rotation about the support rod as the connection rod 32 is extended and retracted. The support rod 33 is attached to frame side walls 20, 21 by rod pin 35. The actuating members 30 are operated either simultaneously or individually and extend and retract movement of the elongate members 40. The actuators 30 may be activated by a solenoid in the actuator (power) means 36 as shown in FIG. 5 or in the control unit 50.

A control unit 50 for regulating the movement of the elongated members 40 and determining the number of revolutions of the elongate members is provided. The control unit 50 includes a speed regulating means, gauge 53 for adjusting the speed of the elongated members. The control unit 50 also includes means 54 for recording the number of oscillations applied to the elongated members sufficient to determine damage to a seam. The control unit 50 has a power supply 51 and a power cord 52 attached to the supply. The unit is operated by off/on switch 55. Port 56 is an air supply for the actuators 30 and air is passed through supply tube 57 to the air pressure supply manifold 58. The oscillating speed is shown on gauge 53. The number of cycles executed is displayed by the revolution counter 54 on the control unit 50.

In an alternative embodiment, two light springs (not shown) are placed on each end of rod 41 within the frame sides to apply light pressure on elongate members 40 to generate wear on the seams (the flat seams as well as the edge seams of the test sample (the glove)), i.e., the pressure between elongate member 40 is increased by the springs. The springs must be light to prevent excessive or "quick" wear of the seams in the test sample. The amount of pressure on the springs may be adjustable. This would require threaded ends on the rod and a nut to compress the spring. But in most applications, light constant (non-adjustable) pressure is recommended.

Using the interactive display the operator inputs the amount of cycles to be executed on the sample. The device then executes the entered amount of cycles by rubbing the seams against one another and against the fabric. Then the wear is compared to a "pass" or "fail" sample for evaluation of competency of the seam, including the durability properties such as separation of filaments and aesthetic damage. It is also possible to set the device for unlimited amount of cycles. In this case, the device is stopped manually by the operator. The amount of cycles executed is displayed by the counter on the control unit. In this case, the number of cycles necessary to achieve full destruction of the seams would be recorded.

The invention also provides a method for testing the seam abrasion of a garment seam, such as a glove, comprising placing a plurality of moveable finger-like elongate members for supporting a garment when said garment is placed thereon; oscillating said elongate members by imparting extending and retracting movement to said elongated member; controlling said oscillated elongate members by regulating the movement of said elongated members; and determining the amount of wear on the seam of said garment. The elongate members may be moved simultaneously or individually.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A testing device for testing the abrasion of the seams of a garment comprising:
    (a) a frame for housing a plurality of actuators;
    (b) a plurality of moveable finger-like elongate members for supporting a garment when said garment is placed on said members;
    (c) a connection rod from each of said actuators extends through an opening in said frame and is attached to one of said elongate members for imparting extending and retracting movement to said elongate member;
    (d) power means for activating said actuator; and
    (e) a control unit for regulating the movement of said elongate members.

2. The seam testing device according to claim 1 wherein said frame further comprises a front wall, a rear wall, a pair of side walls, a base and a cover.

3. The seam testing device according to claim 1 wherein said power means is an electrically operated means.

4. The seam testing device according to claim 1 wherein said power means is a hydraulically operated actuator.

5. The seam testing device according to claim 1 wherein said control unit includes a speed regulating means for adjusting the speed of the elongate members.

6. The seam testing device according to claim 1 wherein said control unit includes means for recording the number of oscillations applied to said elongate members sufficient to determine damage to a seam.

7. The seam testing device according to claim 1 wherein said power means is a pneumatically operated actuator.

8. The seam testing device according to claim 7 wherein said pneumatic actuator includes a piston and rod.

9. A method for testing seam abrasion of a sewn seam comprising
    placing a garment on a plurality of moveable finger-like elongate members for supporting said garment;
    oscillating said elongate members by imparting extending and retracting movement to said elongated member;
    controlling said oscillated elongate members by regulating the movement of said elongated members; and
    determining the amount of wear on the seam of said garment.

10. The method for testing seam abrasion according to claim 9 wherein said plurality of moveable elongate members may be moved individually.

11. The method for testing seam abrasion according to claim 10 wherein said garment is tested for specific properties such as separation of filament and aesthetic damage.

* * * * *